United States Patent
Hovis et al.

(10) Patent No.: US 7,446,238 B2
(45) Date of Patent: Nov. 4, 2008

(54) ALKYLATION PROCESS WITH RECONTACTING IN SETTLER

(75) Inventors: Keith W. Hovis, Stillwater, OK (US); Bruce B. Randolph, Bartlesville, OK (US)

(73) Assignee: UOP LLC, Des Plaines, IL (US)

( * ) Notice: Subject to any disclaimer, the term of this patent is extended or adjusted under 35 U.S.C. 154(b) by 804 days.

(21) Appl. No.: 11/047,514

(22) Filed: Jan. 31, 2005

(65) Prior Publication Data

US 2006/0173231 A1    Aug. 3, 2006

(51) Int. Cl.
*C07C 2/60* (2006.01)
(52) U.S. Cl. .................. 585/723; 585/724; 585/730
(58) Field of Classification Search ........... 585/723, 585/724, 730
See application file for complete search history.

(56) References Cited

U.S. PATENT DOCUMENTS

| | | | |
|---|---|---|---|
| 2,417,106 A | 3/1947 | Frey | 260/683.4 |
| 2,817,692 A | 12/1957 | Penick et al. | 260/683.4 |
| 3,206,524 A | 9/1965 | Plaster | 260/683.42 |
| 3,249,650 A | 5/1966 | Fenske | 260/683.48 |
| 3,607,970 A | 9/1971 | Borst | 260/683.48 |
| 4,677,244 A | 6/1987 | Hachmuth et al. | 585/701 |
| 5,068,448 A | 11/1991 | Lindley et al. | 568/319 |
| 5,185,469 A | 2/1993 | Lindley et al. | 568/319 |
| 5,185,487 A | 2/1993 | Love et al. | 585/449 |
| 6,426,441 B1 | 7/2002 | Randolph et al. | 585/712 |
| 6,858,770 B2 | 2/2005 | Smith, Jr. et al. | 585/720 |

*Primary Examiner*—Thuan Dinh Dang
(74) *Attorney, Agent, or Firm*—James C Paschall

(57) ABSTRACT

A system and/or process for decreasing the level of at least one organic fluoride present in a hydrocarbon phase contained in an alkylation settler by contacting the hydrocarbon phase with an HF containing stream, containing greater than about 80 wt. % and less than about 94 wt. % HF, in the intermediate portion of the settler which contains at least one tray system, with each tray system comprising a perforated tray defining a plurality of perforations and a layer of packing below the perforated tray, are disclosed.

16 Claims, 2 Drawing Sheets

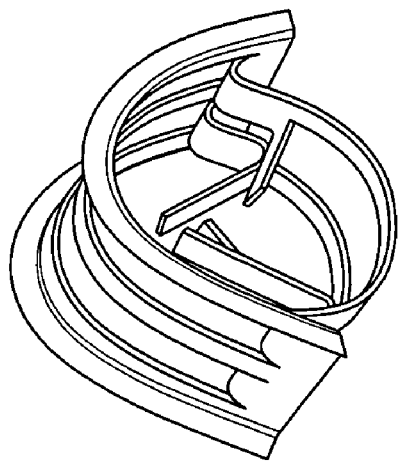
FIG. 3(c)
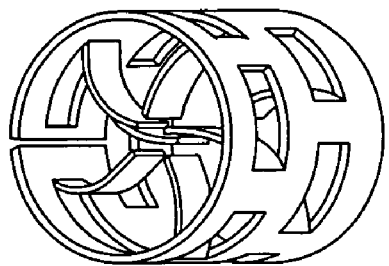
FIG. 3(f)
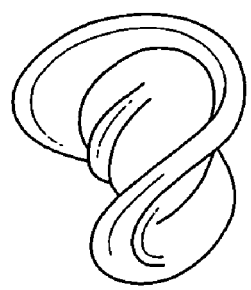
FIG. 3(b)
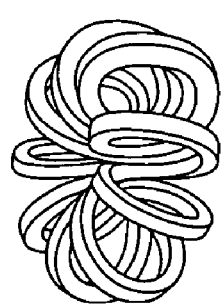
FIG. 3(e)
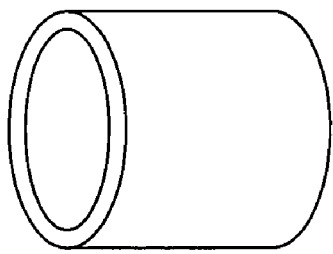
FIG. 3(a)
FIG. 3(d)

ALKYLATION PROCESS WITH RECONTACTING IN SETTLER

The present invention relates to a method and/or system for the alkylation of an olefin with an isoparaffin utilizing an acidic catalyst mixture. In another aspect, this invention relates to a method of reducing the concentration of organic fluorides in an alkylate product.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the reaction mixture to separate the catalyst from the hydrocarbons, thereby forming a catalyst phase and a hydrocarbon phase. The hydrocarbon phase is further separated, for example, by fractionation, to recover the separate product streams. Normally, the hydrocarbon phase of the alkylation process contains hydrocarbons having five to ten carbon atoms per molecule. In order to have the highest quality gasoline blending stock, it is preferred for the alkylate hydrocarbons formed in the alkylation process to be highly branched and contain seven to nine carbon atoms per molecule.

It has long been known that recontacting an alkylate stream containing organic fluorides with hydrogen fluoride is an effective method to reduce the concentration of organic fluorides in such alkylate stream. In order to ensure adequate contact of the alkylate stream with the hydrogen fluoride, the industry has most typically chosen to use an eduction system in a separate recontacting vessel wherein hydrogen fluoride is educted into a flowing alkylate stream followed by separation of the alkylate from the hydrogen fluoride by gravity separation.

It is generally desirable to minimize the number of vessels containing hydrogen fluoride which are present in an alkylation unit. Therefore, development of an improved process and/or system for effectively recontacting alkylate with hydrogen fluoride without using an additional hydrogen fluoride containing vessel would be a significant contribution to the art.

BRIEF SUMMARY OF THE INVENTION

It is, thus, an object of the present invention to provide an improved process and/or system for reducing the concentration of organic fluorides in an alkylation product.

A further object of this invention is to provide an improved process and/or system for reducing the concentration of organic fluorides in an alkylation product wherein the alkylate is recontacted with hydrogen fluoride within a settler vessel allowing the HF used for recontacting to be de-inventoried with the acid catalyst in the settler vessel in the event a rapid acid transfer is required.

In accordance with a first embodiment of the present invention, a system is provided including the following:

a) an alkylation reactor;
b) a settler, having an upper portion, an intermediate portion, and a lower portion wherein the intermediate portion contains at least one tray system comprising a perforated tray defining a plurality of perforations and a layer of packing below the perforated tray;
c) a feed conduit operably related in fluid flow communication to the alkylation reactor;
d) a settler feed conduit operably related in fluid flow communication to the alkylation reactor and to the intermediate portion of the settler at a location below the lower-most tray system;
e) an HF feed conduit operably related in fluid flow communication to the intermediate portion of the settler at a location above the upper-most tray system;
f) an alkylate containing product conduit operably related in fluid flow communication to the upper portion of the settler; and
g) an alkylation catalyst conduit operably related in fluid flow communication to the lower portion of the settler and to the alkylation reactor.

In accordance with a second embodiment of the present invention, a process is provided including the following steps:

a) contacting a hydrocarbon feedstock comprising an olefin and an isoparaffin with a catalyst comprising hydrogen fluoride in an alkylation reaction zone to thereby produce alkylation of at least a portion of the olefins and isoparaffins in the form of an alkylation reaction effluent;
b) providing a settler, having an upper portion, an intermediate portion, and a lower portion wherein the intermediate portion contains at least one tray system comprising a perforated tray defining a plurality of perforations and a layer of packing below the perforated tray;
c) passing the alkylation reaction effluent from the alkylation reaction zone to the intermediate portion of the settler at a location below the lower-most tray system and permitting a phase separation to occur so as to produce a catalyst phase and to produce a hydrocarbon phase comprising alkylate and organic fluorides;
d) passing an HF containing stream comprising greater than about 80 wt. % and less than about 94 wt. % hydrogen fluoride to the intermediate portion of the settler at a location above the upper-most tray system;
e) permitting at least a portion of the hydrocarbon phase to coalesce under each perforated tray thereby providing a hydrocarbon layer under each perforated tray enabling a steady state volume of hydrogen fluoride to collect on the top surface of each perforated tray;
f) for each of the tray systems, permitting at least a portion of the hydrocarbon layer to pass up through the perforated tray in the form of droplets for contact with the steady state volume of hydrogen fluoride;
g) permitting a treated hydrocarbon phase to pass up out of the intermediate portion of the settler; and wherein the cumulative contact time of the hydrocarbon phase with hydrogen fluoride contained in the steady state volumes of hydrogen fluoride in the intermediate portion of the settler is greater than or equal to about 0.5 seconds, and wherein the treated hydrocarbon phase contains less organic fluorides than the hydrocarbon phase;
h) removing the treated hydrocarbon phase from the upper portion of the settler;
i) removing the catalyst phase from the lower portion of the settler; and
j) using a portion of the catalyst phase as at least a portion of the catalyst in the alkylation reaction zone.

BRIEF DESCRIPTION OF THE DRAWING

FIGS. 3 (a)-(f) are perspective views each illustrating an alternative configuration of packing elements useful as packing in the present invention.

DETAILED DESCRIPTION OF THE INVENTION

Figure 2:
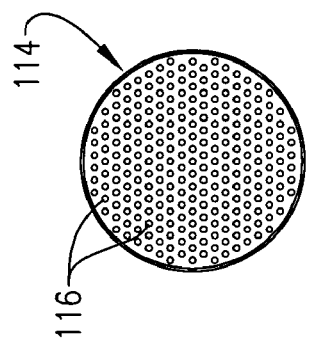
FIG. 2 is a section taken across line 2-2 of the simplified schematic flow diagram of FIG. 1.

According to the first embodiment of the present invention, the system of the present invention will be described with reference to the FIGS. 1 and 2.

Figure 1:
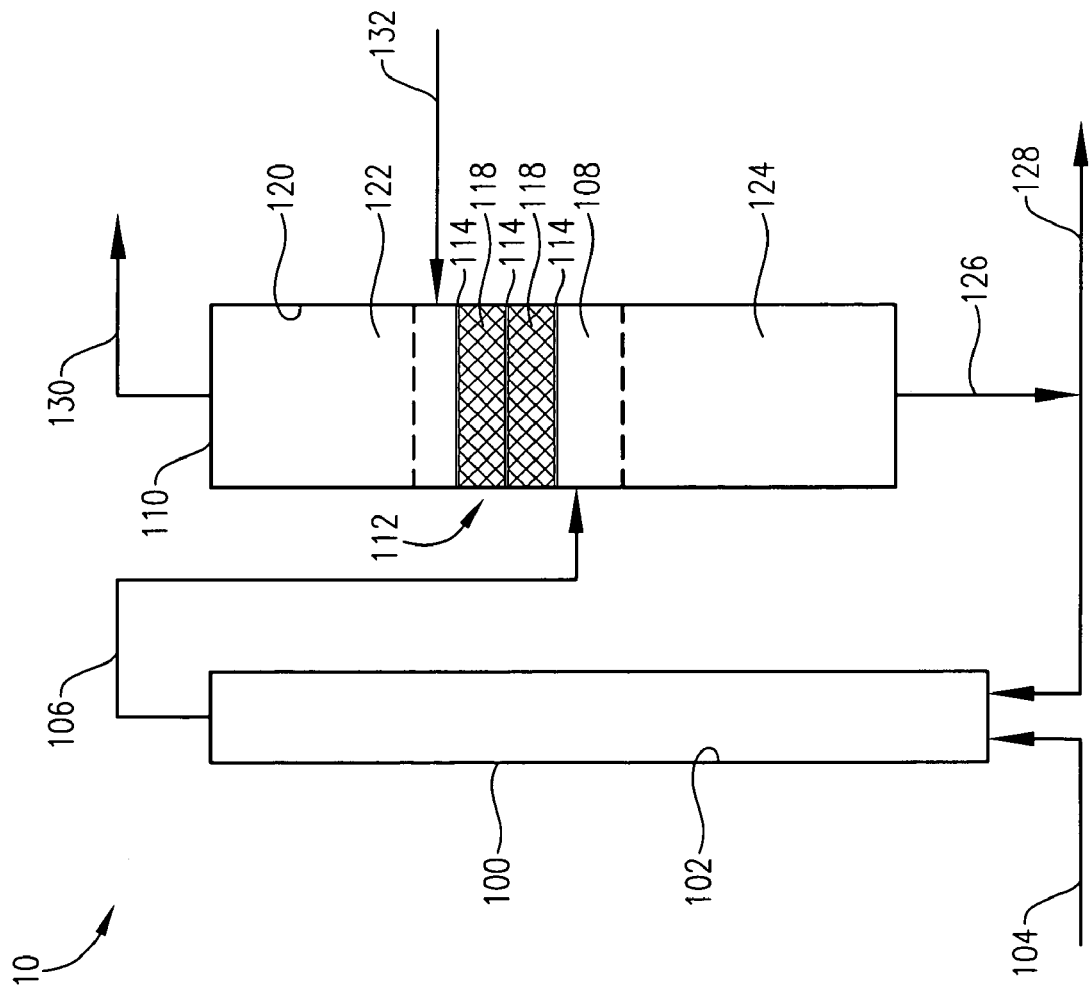
FIG. 1 is a simplified schematic flow diagram presenting an embodiment of the present invention.

Referring to the FIG. 1, therein is illustrated the inventive system or apparatus 10 including an alkylation reactor 100 having an inside wall 102 which defines an alkyaltion reaction zone. The alkylation reactor 100 is operably related by connection in fluid flow communication to a feed conduit 104 for introducing a hydrocarbon feedstock into the alkylation reaction zone. The alkylation reactor 100 provides means for alkylating at least a portion of the hydrocarbon feedstock to thereby produce alkylation of at least a portion of the olefins and isoparaffins in the form of an alkylation reaction effluent.

The alkylation reactor 100 is operably related by connection in fluid flow communication via a settler feed conduit 106 to an intermediate portion 108 of a settler 110. Settler feed conduit 106 is for removing the alkyation reaction effluent from alkylation reactor 100 and for introducing the alkylation reaction effluent into intermediate portion 108 of settler 110 at a location below the lower-most tray system 112 contained in intermediate portion 108. Intermediate portion 108 contains at least one tray system 112 and each tray system 112 comprises, consists of, or consists essentially of a perforated tray 114 defining a plurality of perforations 116 (as shown generally in FIG. 2) and a layer of packing 118 below each of the perforated trays 114. Packing elements useful as packing 118 can be selected from the group consisting of pall rings, raschig rings, berl saddles, intalox saddles, tellrettes, and combinations of any two or more thereof and are depicted in FIGS. 3 (a)-(f). Packing 118 can also comprise structured packing defining multiple fluid flow channels. Intermediate portion 110 preferably contains at least two tray systems 114; and more preferably contains at least three tray systems. Settler 110 also has an inside wall 120 which defines a settling zone, having an upper portion 122, intermediate portion 108, and a lower portion 124. The lower portion 124 of settler 110 is operably related by connection in fluid flow communication, via an alkylation catalyst conduit 126, with alkylation reactor 100 for returning at least a portion of the catalyst phase contained in lower portion 124 to alkylation reactor 100 for use as at least a portion of the catalyst. Conduit 126 is optionally operably related by connection in fluid flow communication to a conduit 128 for removal of a portion of the catalyst phase for regeneration downstream. Upper portion 122 of settler 110 is operably related by connection in fluid flow communication to an alkylate containing product conduit 130 for removing a portion of the hydrocarbon phase contained in upper portion 122 of settler 110 for further processing and/or fractionation downstream. An HF feed conduit 132 is operably related by connection in fluid flow communication to intermediate portion 108 of settler 110 at a location above the upper-most tray system 112 for introducing an HF containing feed to intermediate portion 108.

According to the second embodiment of the present invention, the hydrocarbon feedstock, comprises, consists of, or consists essentially of an olefin and an isoparaffin. The olefin can be selected from the group consisting of propene, an olefin containing four carbon atoms per molecule (butenes), an olefin containing 5 carbon atoms per molecule (pentenes), and combinations of any two or more thereof. Preferably the olefin contains four carbon atoms per molecule. The isoparaffin can be selected from the group consisting of an isoparaffin containing four carbon atoms per molecule, an isoparaffin containing 5 carbon atoms per molecule, and combinations of any two or more thereof. Preferably, the isoparaffin is isobutane.

The catalyst useful in the process can comprise, consist of, or consist essentially of hydrogen fluoride. The catalyst can also comprise, consist of, or consist essentially of hydrogen fluoride and water. Additionally, the catalyst can also comprise, consist of, or consist essentially of hydrogen fluoride and a volatility reducing additive. Furthermore, the catalyst can also comprise, consist of, or consist essentially of hydrogen fluoride, a volatility reducing additive, and water.

The volatility reducing additive can be any compound effective in reducing the volatility of a mixture resulting from the addition of the volatility reducing additive to hydrofluoric acid. More particularly, the volatility reducing additive can be a compound selected from the group consisting of sulfone, ammonia, methylamines, ethylamines, propylamines, butylamines, pentylamines, pyridine, alkylpryidines, melamine, hexamethylene-tetramine and the like, and combinations of any two or more thereof.

The sulfones suitable for use in this invention are the sulfones of the general formula

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfolane.

The hydrocarbon feedstock is contacted with the catalyst in the alkylation reaction zone to thereby produce alkylation of at least a portion of the olefins and isoparaffins in the form of an alkylation reaction effluent. The alkylation reaction effluent is then passed from the alkylation reaction zone to the intermediate portion of the settler, as previously described in the first embodiment, at a location below the lower-most tray system. A phase separation then occurs producing a catalyst phase and a hydrocarbon phase comprising alkylate and organic fluorides. The alkylate generally comprises alkylated hydrocarbons having from 5 to 20 carbon atoms per molecule, unreacted branched chain paraffin hydrocarbons, and isopentane. The organic fluorides are present in the hydrocarbon phase generally in the range of from about 150 ppmw to about 10,000 ppmw, based on the total weight of the hydrocarbon phase. More typically, the concentration of the organic fluorides is in the range of from about 200 ppmw to about 1,000 ppmw; and most typically from 250 ppmw to 500 ppmw, based on the total weight of the hydrocarbon phase.

An HF containing stream comprising greater than about 80 wt. % and less than about 94 wt. % hydrogen fluoride, preferably greater than about 85 wt. % and less than about 94 wt.

%, and most preferably greater than about 85 wt. % and less than about 90 wt. % hydrogen fluoride, is passed to the intermediate portion of the settler at a location above the uppermost tray system. At least a portion of the hydrocarbon phase coalesces under each of the perforated trays of the tray systems thereby providing a hydrocarbon layer under each of the perforated trays enabling a steady state volume of hydrogen fluoride to collect on the top surface of each of the perforated trays. The height of such steady state volumes of hydrogen fluoride can range from about 2 inches to about 22 inches, preferably from about 4 to about 8 inches above the top surfaces of each of the perforated trays.

For each of the tray systems, at least a portion of the hydrocarbon layer accumulated below the perforated tray is allowed to pass up through the perforated tray in the form of droplets for contact with the steady state volume of hydrogen fluoride on top of the perforated tray. The plurality of perforations in each of the perforated trays are defined such that the droplets formed from the hydrocarbon layer have a Sauter mean diameter greater than or equal to about 250 micrometers and less than or equal to about 5000 micrometers, preferably greater than or equal to about 1500 micrometers and less than or equal to about 2500 micrometers.

A treated hydrocarbon phase passes up out of the intermediate portion of the settler into the upper portion of the settler. The cumulative contact time of the hydrocarbon phase with the hydrogen fluoride contained in the steady state volumes of hydrogen fluoride in the intermediate portion of the settler is greater than or equal to about 0.5 seconds, preferably greater than or equal to about 0.5 seconds and less than or equal to about 2.5 seconds, and more preferably greater than or equal to about 0.5 seconds and less than or equal to about 2.0 seconds. The treated hydrocarbon phase contains less organic fluoride than the hydrocarbon phase. The treated hydrocarbon phase is removed from the upper portion of the settler for downstream processing and blending. The catalyst phase is removed from the lower portion of the settler and a portion of the catalyst phase is used as at least a portion of the catalyst in the alkylation reaction zone, with the balance sent downstream for catalyst regeneration.

The following example is provided to further illustrate this invention and is not to be considered as unduly limiting the scope of this invention.

EXAMPLE

The feeds used in these runs were authentic refinery samples of either a total settler effluent sample or an alkylate sample. The reactor(s) used were one inch diameter Monel® schedule 40 pipe of either eight or sixteen inch lengths. The diameters of the feed nozzles used were either 0.010; 0.028 or 0.061 inch with a 0° spray angle. The acid phase was a 99% hydrogen fluoride/1% water blend, circulated with a magnetically driven gear pump. Initial Run A was designed as a base case with a target residence time of 1.5 seconds and nominal 2000 μm Sauter mean diameter (SMD) droplets. All Runs were conducted at 100±2° F. For each Run, the hydrocarbon feed was passed up through the nozzle, creating droplets, which then passed through the eight or sixteen inch layer of acid phase whereupon samples of the treated hydrocarbons were collected and analyzed by gas chromatography (GC).

The results for each Run are presented in the Table 1 below.

TABLE I

| | | Run | | | | | | | | |
|---|---|---|---|---|---|---|---|---|---|---|
| | | A | | | B | | C | | D | |
| Reactor Length, inches | | 8 | | | 8 | | 16 | | 8 | |
| Nozzle Diameter, inches | | 0.028 | | | 0.010 | | 0.028 | | 0.061 | |
| Estimated Droplet SMD, μm | Feed | 231 ~2000 | | | 277 <500 | Feed | 255 2000 | | 255 >3000 | |
| Component | (A & B) | 5 hrs | 22 hrs | 46 hrs. | 26 hrs. | (C & D) | 5 hrs | 23 hrs. | 7 hrs. | 13.75 hrs |
| Lights[1] | 0.04 | 0.05 | 0.02 | 0.02 | 0.01 | 0.11 | 0.02 | 0.03 | 0.21 | 0.03 |
| Propane | 8.37 | 8.16 | 8.16 | 8.06 | 7.81 | 8.08 | 8.43 | 8.03 | 7.76 | 6.95 |
| Isobutane | 55.13 | 53.31 | 52.95 | 52.76 | 53.61 | 54.64 | 52.87 | 53.70 | 53.23 | 52.88 |
| n-butane | 8.22 | 8.20 | 8.08 | 8.16 | 8.26 | 8.08 | 8.13 | 8.30 | 8.20 | 8.32 |
| Olefin | 0.08 | 0 | 0 | 0 | 0 | 0.08 | 0 | 0 | 0 | 0 |
| HC4F | 0.11 | 0 | 0 | 0 | 0 | 0.11 | 0 | 0 | 0 | 0 |
| HC3F | 0.25 | 0 | 0 | 0 | 0 | 0.24 | 0 | 0 | 0 | 0 |
| i-pentane | 3.62 | 4.31 | 4.32 | 4.34 | 4.39 | 3.58 | 5.41 | 5.30 | 4.44 | 4.59 |
| n-pentane | 0.04 | 0.04 | 0.04 | 0.04 | 0.04 | 0.04 | 0.05 | 0.05 | 0.04 | 0.05 |
| 2,2-dimethylbutane | 0 | 0 | 0 | 0 | 0 | 0 | 0.02 | 0 | 0 | 0 |
| 2,3-dimethylbutane | 1.38 | 1.57 | 1.56 | 1.61 | 1.66 | 1.39 | 1.51 | 1.60 | 1.57 | 1.64 |
| 2-methylpentane | 0.24 | 0.40 | 0.42 | 0.41 | 0.42 | 0.25 | 0.56 | 0.56 | 0.41 | 0.42 |
| 3-methylpentane | 0.11 | 0.18 | 0.19 | 0.19 | 0.19 | 0.11 | 0.25 | 0.25 | 0.18 | 0.19 |
| 2,4-dimethylpentane | 2.49 | 3.14 | 3.18 | 3.20 | 3.76 | 2.54 | 2.75 | 2.99 | 2.92 | 3.08 |
| 2,2,3-trimethylbutane | 0.02 | 0.03 | 0.04 | 0.03 | 0.04 | 0.03 | 0.04 | 0.04 | 0.04 | 0 |
| 2-methylhexane | 0.10 | 0.20 | 0.21 | 0.20 | 0.23 | 0.10 | 0.25 | 0.26 | 0.19 | 0.19 |
| 2,3-dimethylpentane | 6.56 | 6.06 | 6.02 | 6.18 | 5.19 | 6.69 | 5.53 | 5.30 | 6.24 | 6.60 |
| 3-methylhexane | 0.08 | 0.14 | 0.16 | 0.15 | 0.16 | 0.08 | 0.18 | 0.19 | 0.14 | 0.14 |
| 2,2,4-trimethylpentane | 4.60 | 4.75 | 4.84 | 4.93 | 4.86 | 4.75 | 4.36 | 4.35 | 4.82 | 5.09 |
| 2,5-dimethylhexane | 0.54 | 0.68 | 0.72 | 0.71 | 0.76 | 0.57 | 0.73 | 0.75 | 0.69 | 0.72 |
| 2,4-dimethylhexane | 0.66 | 0.77 | 0.81 | 0.80 | 0.83 | 0.69 | 0.80 | 0.81 | 0.79 | 0.82 |
| 2,2,3-trimethylpentane | 0.08 | 0.13 | 0.14 | 0.14 | 0.14 | 0.09 | 0.16 | 0.17 | 0.14 | 0.14 |
| 2,3,4-trimethylpentane | 1.88 | 1.77 | 1.79 | 1.82 | 1.50 | 1.96 | 1.68 | 1.56 | 1.85 | 1.95 |
| 2,3,3-trimethylpentane | 0.82 | 0.91 | 0.95 | 0.95 | 0.99 | 0.86 | 0.85 | 0.86 | 0.93 | 0.96 |
| 2,3-dimethylhexane | 0.63 | 0.63 | 0.65 | 0.65 | 0.55 | 0.66 | 0.63 | 0.60 | 0.66 | 0.69 |
| 2-methylheptane | 0 | 0 | 0 | 0 | 0. | 0 | 0.05 | 0.05 | 0 | 0 |

TABLE I-continued

| | | Run | | | | | | | | |
|---|---|---|---|---|---|---|---|---|---|---|
| | | A | | | | B | C | | D | |
| Reactor Length, inches | | 8 | | | | 8 | 16 | | 8 | |
| Nozzle Diameter, inches | | 0.028 | | | | 0.010 | 0.028 | | 0.061 | |
| Estimated Droplet SMD, μm | Feed | ~2000 | | | Feed | <500 | 2000 | | >3000 | |
| Component | (A & B) | 5 hrs | 22 hrs | 46 hrs. | 26 hrs. | (C & D) | 5 hrs. | 23 hrs. | 7 hrs. | 13.75 hrs |
| 3,4-dimethylhexane | 0.08 | 0.09 | 0.09 | 0.09 | 0.10 | 0.08 | 0.09 | 0.09 | 0.09 | 0.09 |
| 3-methylheptane | 0 | 0 | 0 | 0 | 0 | 0 | 0.04 | 0 | 0 | 0 |
| 2,2,5-trimethylhexane | 0.72 | 0.92 | 0.98 | 0.96 | 1.03 | 0.77 | 1.00 | 1.03 | 0.95 | 0.99 |
| Residue | 3.15 | 3.56 | 3.68 | 3.60 | 3.47 | 3.42 | 3.61 | 3.13 | 3.51 | 3.47 |
| [Total] | 100 | 100 | 100 | 100 | 100 | 100 | 100 | 100 | 100 | 100 |
| HC4F ppmw F by gc | 354 | 0 | 0 | 0 | 0 | 354 | 0 | 0 | 0 | 0 |
| HC3F ppmw F by gc | 1125 | 0 | 0 | 0 | 0 | 1090 | 0 | 0 | 0 | 0 |

[1]unidentified C1-C4 components

The results from the GC analysis showed a complete absence of detectable levels of 2-fluoropropane (HC3F) and 2-fluoro-2-methylpropane (HC4F). The detection limit for alkyl fluorides for the GC is believed to be around 15 ppmw. It was determined that the peak corresponding to HC4F was potentially masked by the n-butane signal. Similarly, the HC3F peak, at these low concentrations of HC3F relative to isobutane, was probably just not observable.

Thus, it was decided to boil off the isobutane from the samples and analyze the stabilized alkylate product for alkylate range organic fluorides (primarily $HC_5F$) using an electrolytic conductivity detection (ELCD) instrument. This instrument responds only to total fluoride with no speciation. The boiled off samples (both feed and product) were re-analyzed using GC to determine HC3F and HC4F levels (if any), and the concentration of $C_5+$ organic fluorides was determined based on the new GC data and the ELCD total fluoride values. The research octane number (RON) and motor octane number (MON) were calculated from the GC data based on the $C_5+$ components only for the feed and products for each Run. The results of the GC and ELCD analyses and the RON and MON estimations are presented in Table II below.

TABLE II

| | | Run | | | |
|---|---|---|---|---|---|
| | | A | B | C | D |
| Reactor Length, inches | | 8 | 8 | 16 | 8 |
| Nozzle Diameter, inches | | 0.028 | 0.01 | 0.028 | 0.061 |
| Feed Rate, mL/hr | | 231 | 277 | 255 | 255 |
| Estimated Droplet SMD, μm | | ~2000 | <500 | 2000 | >3000 |
| ELCD Results: Weathered Samples Component | Feed | 5 hrs  22 hrs  46 hrs | 26 hrs | 5 hrs  23 hrs | 7 hrs  13.75 hrs |
| Total F, ppmw (by ELCD) | 177 | 69.9  73.3  52 | 51.6 | 35.9  42.8 | 80.6  63.2 |
| C3F, ppmw (by GC) | 15 | 0  0  0 | 0 | 0  0 | 0  0 |
| C4F, ppmw (by GC) | 22 | 0  0  0 | 0 | 0  0 | 0  0 |
| C5F, ppmw[1] | 140 | 69.9  73.3  52 | 51.6 | 35.9  42.8 | 80.6  63.2 |
| % Total Alkyl Fluoride Conversion | | 60.5%  58.6%  70.6% | 70.8% | 79.7%  75.8% | 54.5%  64.3 |
| | Feed | Average | 26 hrs. | Average | Average |
| RONgc | 90.80 | 90.06 | 89.55 | 89.41 | 90.01 |
| MONgc | 89.06 | 88.43 | 88.04 | 87.78 | 88.39 |
| Delta RON | | −0.74 | −1.25 | −1.02 | −0.42 |
| Delta MON | | −0.63 | −1.02 | −1.06 | −0.45 |

[1]calculated by subtracting HC3F and HC4F concentrations from the ELCD total result.

As can be seen from Table II, the conversion of HC5F fluorides was higher in Run B wherein the droplet SMD was <500 as compared to the HC5F conversion in Run A wherein the droplet SMD was ~2000. However, the delta RON and delta MON for Run B were significantly higher than for Run A. Thus, while smaller droplets appear to result in greater HC5F conversion, there is a corresponding octane reduction for the alkylate which would likely be unacceptable to most refiners.

Also, the conversion of HC5F fluorides was higher in Run C wherein the reactor length was sixteen inches as compared to the HC5F conversion in Run A wherein the reactor length was eight inches. However, the delta RON and delta MON for Run C were significantly higher than for Run A. Thus, while longer contact times appear to result in greater HC5F conversion, there is a corresponding octane reduction for the alkylate which would likely be unacceptable to most refiners.

In addition, the conversion of HC5F fluorides was on average lower in Run D wherein the droplet SMD was>3000 as compared to the HC5F conversion in Run A wherein the droplet SMD was~2000. The delta RON and delta MON for Run D were lower than for Run A. Thus, while larger droplets appear to result in less alkylate octane degradation, the corresponding reduction in HC5F conversion would make the use of such larger droplets impractical.

While this invention has been described in detail for the purpose of illustration, it should not be construed as limited thereby but intended to cover all changes and modifications within the spirit and scope thereof.

That which is claimed is:

1. A process comprising:
    a) contacting a hydrocarbon feedstock comprising an olefin and an isoparaffin with a catalyst comprising hydrogen fluoride in an alkylation reaction zone to thereby produce alkylation of at least a portion of the olefins and isoparaffins in the form of an alkylation reaction effluent;
    b) providing a settler, having an upper portion, an intermediate portion, and a lower portion wherein said intermediate portion contains at least one tray system comprising a perforated tray defining a plurality of perforations and a layer of packing below said perforated tray;
    c) passing said alkylation reaction effluent from said alkylation reaction zone to said intermediate portion of said settler at a location below said lower-most tray system and permitting a phase separation to occur so as to produce a catalyst phase and to produce a hydrocarbon phase comprising alkylate and organic fluorides;
    d) passing an HF containing stream comprising greater than about 80 wt. % and less than about 94 wt. % hydrogen fluoride to said intermediate portion of said settler at a location above said upper-most tray system;
    e) permitting at least a portion of said hydrocarbon phase to coalesce under each said perforated tray thereby providing a hydrocarbon layer under each said perforated tray enabling a steady state volume of hydrogen fluoride to collect on the top surface of each said perforated tray;
    f) for each of said tray systems, permitting at least a portion of said hydrocarbon layer to pass up through said perforated tray in the form of droplets for contact with said steady state volume of hydrogen fluoride;
    g) permitting a treated hydrocarbon phase to pass up out of said intermediate portion of said settler; and wherein the cumulative contact time of said hydrocarbon phase with hydrogen fluoride contained in said steady state volumes of hydrogen fluoride in said intermediate portion of said settler is greater than or equal to about 0.5 seconds, and wherein said treated hydrocarbon phase contains less organic fluorides than said hydrocarbon phase;
    h) removing said treated hydrocarbon phase from said upper portion of said settler;
    i) removing said catalyst phase from said lower portion of said settler; and
    j) using a portion of said catalyst phase as at least a portion of said catalyst in said alkylation reaction zone.

2. A process as recited in claim 1 wherein said catalyst is further characterized to comprise a volatility reducing additive.

3. A process as recited in claim 2 wherein said volatility reducing additive comprises a sulfone.

4. A process as recited in claim 2 wherein said volatility reducing additive comprises sulfolane.

5. A process as recited in claim 1 wherein said intermediate portion contains at least two of said tray systems.

6. A process as recited in claim 1 wherein said intermediate portion contains at least three of said tray systems.

7. A process as recited in claim 1 wherein said packing is selected from the group consisting of pall rings, raschig rings, berl saddles, intalox saddles, tellerettes, and combinations of any two or more thereof.

8. A process as recited in claim 1 wherein said packing comprises structured packing defining multiple fluid flow channels.

9. A process as recited in claim 1 wherein said HF containing stream comprises greater than about 85 wt. % and less than about 94 wt. % hydrogen fluoride.

10. A process as recited in claim 1 wherein said HF containing stream comprises greater than about 85 wt. % and less than about 90 wt. % hydrogen fluoride.

11. A process as recited in claim 1 wherein said plurality of perforations in each said perforated tray are defined such that said droplets have a Sauter mean diameter greater than or equal to about 250 µm and less than or equal to about 5000 µm.

12. A process as recited in claim 1 wherein said plurality of perforations in each said perforated tray are defined such that said droplets have a Sauter mean diameter greater than or equal to about 1500 µm and less than or equal to about 2500 µm.

13. A process as recited in claim 1 wherein said cumulative contact time in step g) is greater than or equal to about 0.5 seconds and less than or equal to about 2.5 seconds.

14. A process as recited in claim 1 wherein said cumulative contact time in step g) is greater than or equal to about 0.5 seconds and less than or equal to about 2.0 seconds.

15. A process as recited in claim 1 wherein said olefin is selected from the group consisting of propene, an olefin containing four carbon atoms per molecule, an olefin containing five carbon atoms per molecule, and combinations of any two or more thereof.

16. A process as recited in claim 1 wherein said isoparaffin is selected from the group consisting of an isoparaffin containing four carbon atoms per molecule, an isoparaffin containing five carbon atoms per molecule, and combinations of any two or more thereof.

* * * * *